United States Patent
Uemura

(10) Patent No.: US 9,928,573 B2
(45) Date of Patent: Mar. 27, 2018

(54) BIOLOGICAL SAMPLE MEASURING DEVICE

(71) Applicant: PANASONIC HEALTHCARE HOLDINGS CO., LTD., Minato-Ku, Tokyo (JP)

(72) Inventor: Toyotoshi Uemura, Ehime (JP)

(73) Assignee: Panasonic Healthcare Holdings Co., Ltd., Tokyo (JP)

(*) Notice: Subject to any disclaimer, the term of this patent is extended or adjusted under 35 U.S.C. 154(b) by 339 days.

(21) Appl. No.: 14/360,652

(22) PCT Filed: Dec. 12, 2012

(86) PCT No.: PCT/JP2012/007928
§ 371 (c)(1),
(2) Date: May 27, 2014

(87) PCT Pub. No.: WO2013/099128
PCT Pub. Date: Jul. 4, 2013

(65) Prior Publication Data
US 2014/0320538 A1    Oct. 30, 2014

(30) Foreign Application Priority Data

Dec. 27, 2011  (JP) ................................. 2011-285030
Oct. 22, 2012  (JP) ................................. 2012-232595

(51) Int. Cl.
*G06T 3/60*      (2006.01)
*G01N 33/487*    (2006.01)
(Continued)

(52) U.S. Cl.
CPC .......... *G06T 3/60* (2013.01); *G01N 33/48785* (2013.01); *G06F 3/0485* (2013.01);
(Continued)

(58) Field of Classification Search
None
See application file for complete search history.

(56) References Cited

U.S. PATENT DOCUMENTS 5,982,370 A * 11/1999 Kamper ................ G06F 3/0481
707/999.003
6,281,879 B1 * 8/2001 Graham .............. G06F 3/04812
345/157

(Continued)

FOREIGN PATENT DOCUMENTS

JP    2002-055753 A    2/2002
JP    2006-072489 A    3/2006
(Continued)

OTHER PUBLICATIONS

Mark S. Hancock, Improving Menu Placement Strategies for Pen Input, 2004, Thesis (Master of Science), University of British Columbia, Vancouver, Canada.*

(Continued)

*Primary Examiner* — Michael J Cobb
(74) *Attorney, Agent, or Firm* — Shinjyu Global IP

(57) ABSTRACT

The controller divides a display of the display component provided to the main body case into a first display area that is disposed on a sensor mounting component side and displays measurement values, and a second display area that is disposed on the opposite side from the sensor mounting component side and displays input buttons. When the acceleration sensor has detected that the orientation of the main body case is inverted in a horizontal direction, the controller rotates a display of the first display area and a display of the second display area 180 degrees within each of these areas.

9 Claims, 6 Drawing Sheets

(51) Int. Cl.
*G06F 3/0488* (2013.01)
*G06F 3/0485* (2013.01)
*G09G 5/00* (2006.01)

(52) U.S. Cl.
CPC ........ *G06F 3/0488* (2013.01); *G06F 3/04883* (2013.01); *G06F 2200/1614* (2013.01); *G06F 2203/04803* (2013.01); *G09G 5/00* (2013.01); *G09G 2340/045* (2013.01); *G09G 2340/0492* (2013.01); *G09G 2340/14* (2013.01)

(56) References Cited

U.S. PATENT DOCUMENTS

| | | | |
|---|---|---|---|
| 7,802,206 B1* | 9/2010 | Davis | H04M 1/274525 345/156 |
| 7,844,301 B2 | 11/2010 | Lee et al. | |
| 8,597,570 B2 | 12/2013 | Terashima et al. | |
| 8,696,597 B2 | 4/2014 | Neel et al. | |
| 9,386,328 B1* | 7/2016 | Crane | H04N 21/4312 |
| 2002/0154168 A1* | 10/2002 | Ijas | G06F 3/0481 715/764 |
| 2002/0196287 A1* | 12/2002 | Taylor | G06F 3/0481 715/792 |
| 2005/0229110 A1* | 10/2005 | Gegner | G06F 3/0481 715/800 |
| 2006/0044283 A1 | 3/2006 | Eri et al. | |
| 2006/0277478 A1* | 12/2006 | Seraji | G06F 3/0481 715/760 |
| 2007/0079284 A1* | 4/2007 | Kim | G06F 17/30572 717/113 |
| 2007/0085759 A1 | 4/2007 | Lee et al. | |
| 2007/0233395 A1 | 10/2007 | Neel et al. | |
| 2008/0024451 A1* | 1/2008 | Aimi | G01C 21/3611 345/168 |
| 2008/0079689 A1* | 4/2008 | Koskinen | G09G 5/00 345/156 |
| 2009/0149717 A1* | 6/2009 | Brauer | G06F 19/3406 600/300 |
| 2009/0177997 A1* | 7/2009 | Do | G06F 17/30899 715/789 |
| 2009/0305317 A1* | 12/2009 | Brauer | C12Q 1/00 435/14 |
| 2010/0007792 A1* | 1/2010 | Kim | H04N 5/44513 348/569 |
| 2010/0198142 A1 | 8/2010 | Sloan et al. | |
| 2010/0262318 A1* | 10/2010 | Ariens | G01C 21/00 701/3 |
| 2010/0281431 A1 | 11/2010 | Kano et al. | |
| 2011/0009813 A1* | 1/2011 | Rankers | A61B 5/15077 604/66 |
| 2011/0032202 A1 | 2/2011 | Aoyagi et al. | |
| 2011/0185308 A1 | 7/2011 | Machida | |
| 2011/0193704 A1* | 8/2011 | Harper | A61B 5/14532 340/573.1 |
| 2011/0257496 A1 | 10/2011 | Terashima et al. | |
| 2011/0257533 A1* | 10/2011 | Nishiyama | A61B 5/14532 600/476 |
| 2013/0021377 A1* | 1/2013 | Doll | G09G 5/14 345/649 |
| 2013/0198685 A1* | 8/2013 | Bernini | G06F 3/0484 715/800 |
| 2014/0013408 A1* | 1/2014 | Ryu | G06F 21/36 726/7 |
| 2014/0046160 A1 | 2/2014 | Terashima et al. | |

FOREIGN PATENT DOCUMENTS

| | | |
|---|---|---|
| JP | 2007-109240 A | 4/2007 |
| JP | 2009-532706 A | 9/2009 |
| JP | 2010-063576 A | 3/2010 |
| JP | 2010-266217 A | 11/2010 |
| JP | 2011-034538 A | 2/2011 |
| JP | 2011-505960 A | 3/2011 |
| JP | 2011-154555 A | 8/2011 |
| JP | 4823342 b2 | 11/2011 |
| JP | 2011-252851 A | 12/2011 |
| JP | 5026597 b2 | 9/2012 |
| WO | 2007/118046 A2 | 10/2007 |
| WO | 2009/075697 A1 | 6/2009 |
| WO | 2009/087992 A1 | 7/2009 |
| WO | 2010/052849 A1 | 5/2010 |

OTHER PUBLICATIONS

International Search Report from PCT/JP2012/007928 dated Jan. 15, 2013.

* cited by examiner

BIOLOGICAL SAMPLE MEASURING DEVICE

PRIORITY

This application claims priority to International Application No. PCT/JP2012/007928, with an international filing date of Dec. 12, 2012 which claims priority to Japanese Patent Application No. 2011-285030 filed on Dec. 27, 2011 and Japanese Patent Application No. 2012-232595 filed on Oct. 22, 2012. The entire disclosures of International Application No. PCT/JP2012/007928 and Japanese Patent Applications No. 2011-285030 and No. 2012-232595 are hereby incorporated herein by reference

TECHNICAL FIELD

The present invention relates to a biological sample measuring device that measures biological information, such as blood glucose levels from blood.

BACKGROUND ART

A conventional biological sample measuring device of this type comprised a cuboid main body case having a sensor mounting component at one end, a measurement component connected to the sensor mounting component inside the main body case, a controller connected to the measurement component, and a rectangular display component provided to the outer surface of the main body case.

Input buttons provided around the outside of display component were then used to perform various kinds of input to the biological sample measuring device (see Patent Literature 1: International Laid-Open Patent Application 2007/118046, for example).

With a conventional biological sample measuring device, mechanical input buttons are disposed around the outside of the display component, but as the functions of biological sample measuring devices have been increasingly sophisticated in recent years, more functions have been assigned to these input buttons. Accordingly, the user cannot intuitively tell which these input buttons are used for, making the device less convenient to use.

In view of this, it is an object of the present invention to improve convenience.

SUMMARY

The present invention comprises a main body case including a sensor mounting component at one end, a measurement component connected to the sensor mounting component inside the main body case, a controller connected to the measurement component, an acceleration sensor connected to the controller and operable to sense an orientation of the main body case, and a touch input-type display component provided to an outer surface of the main body case. The controller divides a display of the display component into a first display area and a second display area, the first display area being disposed on the sensor mounting component side and operable to display a measurement value, and the second display area being disposed on an opposite side from the sensor mounting component side and operable to display an input button. When the acceleration sensor has detected that the orientation of the main body case is inverted in a horizontal direction, the controller rotates a display of the first display area 180 degrees within the first display area, and rotates a display of the second display area 180 degrees within the second display area.

The present invention comprises the display component that is a touch input-type of rectangular display component, and the input buttons are graphically displayed in the second display area of the display component. Accordingly, the user can intuitively grasp functions of the input buttons, making the device more convenient to use.

The second display area in which the input buttons are displayed is disposed on the opposite side from the sensor mounting component side. Accordingly, when the input buttons are being used, the user's fingers, etc., do not touch the sensor where blood is deposited.

Furthermore, when the acceleration sensor within the main body case has detected that the orientation of the main body case is inverted in the horizontal direction, the display of the second display area is rotated 180 degrees within the second display area so that a vertical direction of the display will be in the proper state as seen by the user. That is, since the input buttons are displayed rotated within the second display area, which is the button display area, the input buttons are displayed on the opposite side from the sensor mounting component.

Accordingly, when the user operates the input buttons in the display component, the user's fingers, etc., will not touch the sensor where blood is deposited.

The result of the above is a more convenient device.

DESCRIPTION OF EMBODIMENTS

The biological sample measuring device according to embodiments of the present invention will now be described through reference to the drawings.

First Embodiment

Figure 1A:
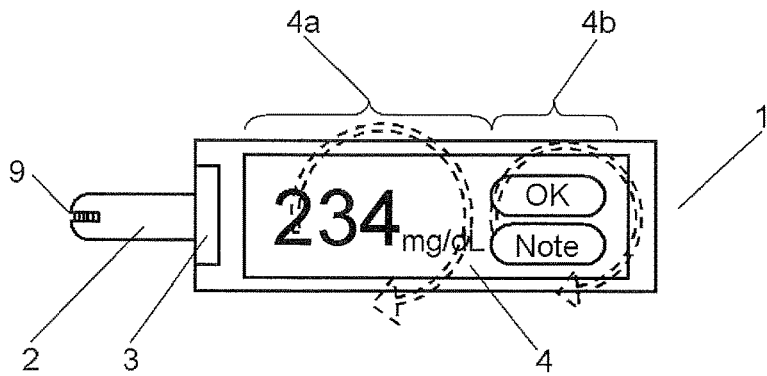
FIG. 1A is a plan view of the biological sample measuring device in a first embodiment of the present invention.
Figure 1B:
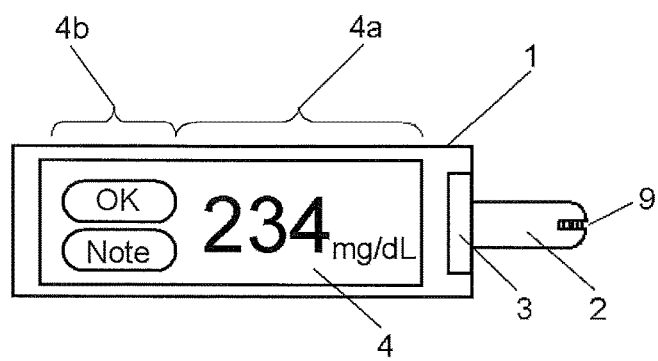
FIG. 1B is a plan view of the biological sample measuring device in the first embodiment of the present invention.
Figure 2:
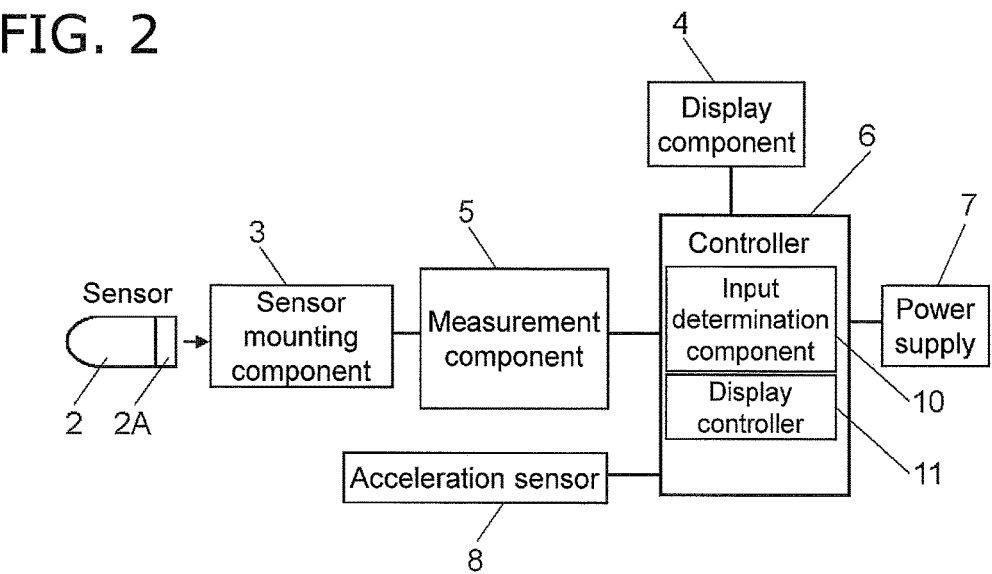
FIG. 2 is a control block diagram of the biological sample measuring device in the first embodiment of the present invention.

As shown in FIGS. 1 and 2, the main body case 1 of a biological sample measuring device that measures blood glucose levels from blood, which is an example of a biological sample measuring device, is formed in a substantially cuboid shape. A sensor mounting component 3 for inserting a connection terminal 2A of a blood glucose level sensor 2, which is an example of a biological sample sensor, is provided at one end of the main body case 1. A rectangular, touch input-type display component 4 is provided over substantially the entire outer surface on the upper face side of the main body case 1. The lengthwise direction of the display component 4 is the same as the lengthwise direction of the main body case 1.

A measurement component 5 is electrically connected to the sensor mounting component 3 inside the main body case 1, and a controller 6 is connected to the measurement component 5. The display component 4, a power supply 7, and an acceleration sensor 8 are connected to the controller 6. The acceleration sensor 8 is a triaxial acceleration sensor, is disposed in the approximate center inside the main body case 1, and senses the orientation of the main body case 1.

When the connection terminal 2A of the blood glucose level sensor 2 is inserted into the sensor mounting component 3, and blood is deposited onto a deposition component 9 at one end of the blood glucose level sensor 2, the blood glucose level is measured by the measurement component 5, and the controller 6 controls the display component 4 so as to display the measured blood glucose level.

The display component 4 has a first display area 4a that is a measurement value display area for displaying measured blood glucose levels, and a second display area 4b that is a button display area for displaying input buttons. The first display area 4a and the second display area 4b are disposed respectively on the left and right in the lengthwise direction of the display component 4. The first display area 4a is disposed on the sensor mounting component 3 side, and the second display area 4b is disposed on the opposite side from the sensor mounting component 3 side. The first display area 4a displays the measured blood glucose level, and therefore has a larger surface area than the second display area 4b.

An example of display will now be described through reference to FIG. 1. A value indicating blood glucose level is displayed as "234 mg/dL" in the first display area 4a (the measurement value display area), and in the second display area 4b (the button display area), an "OK" button is displayed at the top, and a "Note" button at the bottom. As mentioned above, the display component 4 is a touch input type, so when the user touches the "OK" button, for example, an input determination component 10 of the controller 6 determines that the "OK" button has been pressed, and the controller 6 ends measurement. If the user touches the "Note" button, the input determination component 10 of the controller 6 determines that the "Note" button has been pressed, and a measurement history is displayed by the controller 6.

Thus, the display component 4 graphically displays input buttons representing functions corresponding to usage states, in the second display area 4b (the button display area), so the user can intuitively grasp the function of the input buttons, making the device more convenient to use.

Figure 3:
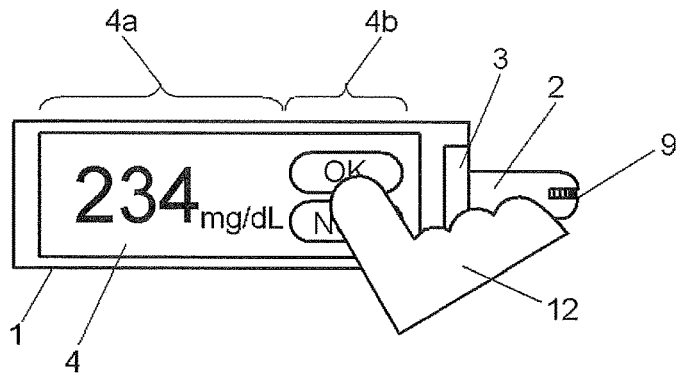
FIG. 3 is a plan view of an example of a problem to be addressed by the biological sample measuring device in the first embodiment of the present invention.

Furthermore, in this embodiment, as discussed above, the second display area 4b of the display component 4 is disposed on the opposite side from the sensor mounting component 3 side. As shown in FIG. 3, if the second display area 4b where an input button is displayed is disposed on the sensor mounting component 3, when the user operates the input button, the hand 12 of the user may accidentally touch the blood glucose level sensor 2 where blood has been deposited. In contrast, in this embodiment, as shown in FIGS. 1A and 1B, since the input buttons are displayed in the second display area 4b, which is disposed on the opposite side from the sensor mounting component 3 side, the user's fingers, etc., will not touch the blood glucose level sensor 2 where blood has been deposited, during use of the input buttons.

As a result, a more convenient biological sample measuring device can be provided.

Also, in this embodiment, if the orientation of the main body case 1 has undergone left-right inversion from the state shown in FIG. 1A to the state shown in FIG. 1B, the acceleration sensor 8 in the main body case 1 detects the left-right inversion of the orientation of the main body case. The controller 6 then receives a signal from the acceleration sensor 8, and controls the display so that the display of blood glucose level in the first display area 4a (measurement value display area) is rotated 180 degrees within the first display area 4a. In addition, the display of the input buttons in the second display area 4b (button display area) rotates 180 degrees within the second display area 4b. Accordingly, the display will be in the correct up and down directional state as seen from the user, and as a result a more convenient biological sample measuring device can be provided.

This operation will be described in more detail through reference to FIGS. 1, 2, and 4.

When the user measures a blood glucose level, first he/she inserts the connection terminal 2A of the blood glucose level sensor 2 into the sensor mounting component 3. If the user is left-handed, he/she punctures his own right hand with a needle (not shown) or the like to draw blood, deposits the blood on the deposition component 9 of the blood glucose level sensor 2 while holding the main body case 1 in his/her left hand, and thereby measures the blood glucose level. However, since the user cannot always puncture just the right hand, he/she may sometimes puncture his/her left hand with the needle, hold the main body case 1 in his/her right hand, and measure the blood glucose level in the state shown in FIG. 1A. In this case, the blood that comes out of the left hand is deposited on the deposition component 9 of the blood glucose level sensor 2, whereupon the measurement component 5 measures the blood glucose level.

Then, a display controller 11 of the controller 6 displays the measured blood glucose level in the first display area 4a, which is the measurement value display area on the sensor mounting component 3 side, and displays input buttons indicating the proper function at this time in the second display area 4b, which is the button display area on the opposite side from the sensor mounting component 3. The displays in the first display area 4a and second display area 4b are carried out properly by the display controller 11.

At this point, since the acceleration sensor 8 inside the main body case 1 is a triaxial acceleration sensor, it determines the orientation of the main body case 1. More specifically, the controller 6 receives a signal from the acceleration sensor 8 and determines the left and right direction of the main body case 1, and puts a display on the display component 4 so that the up and down direction of the display is in the correct state as seen from the user.

Here, a left-handed user who has held the main body case 1 in his/her right hand to measure the blood glucose level will switch the main body case 1 to his/her dominant left hand so that he/she can operate the input buttons in a familiar state. That is, the state in FIG. 1A changes to the state in FIG. 1B, as seen from the user.

The operation of the controller 6 here will be described through reference to the operational flowchart in FIG. 4.

In this embodiment, when the state in FIG. 1A changes to the state in FIG. 1B, that is, when the main body case 1 is rotated 180 degrees so that the display of the display component 4 is flipped horizontally, the controller 6 receives a signal from the acceleration sensor 8 inside the main body case 1, detects the orientation of the main body case 1, and detects that the current orientation of the main body case 1 is inverted right or left (step S1).

When it is determined that the left and right direction has been flipped as seen from the user (step S2), the blood glucose level (measurement value) displayed in the first display area 4a is rotated 180 degrees within the first display area 4a (step S3). In addition, the input buttons displayed in the second display area 4b are rotated 180 degrees within the second display area 4b (step S4), and the orientation confirmation processing is ended (step S5).

Therefore, as shown in FIG. 1B, this embodiment can provide a biological sample measuring device that is more convenient to use because the up and down direction of the display is in the correct state as seen from the user.

At this point, since the display of the input buttons is rotated within the second display area 4b (the button display area), the input buttons are again displayed on the opposite side from the sensor mounting component 3. Therefore, when the user operates an input button, his/her fingers, etc. will not touch the blood glucose level sensor 2 where the blood has been deposited, making the device more convenient to use.

Figure 4:
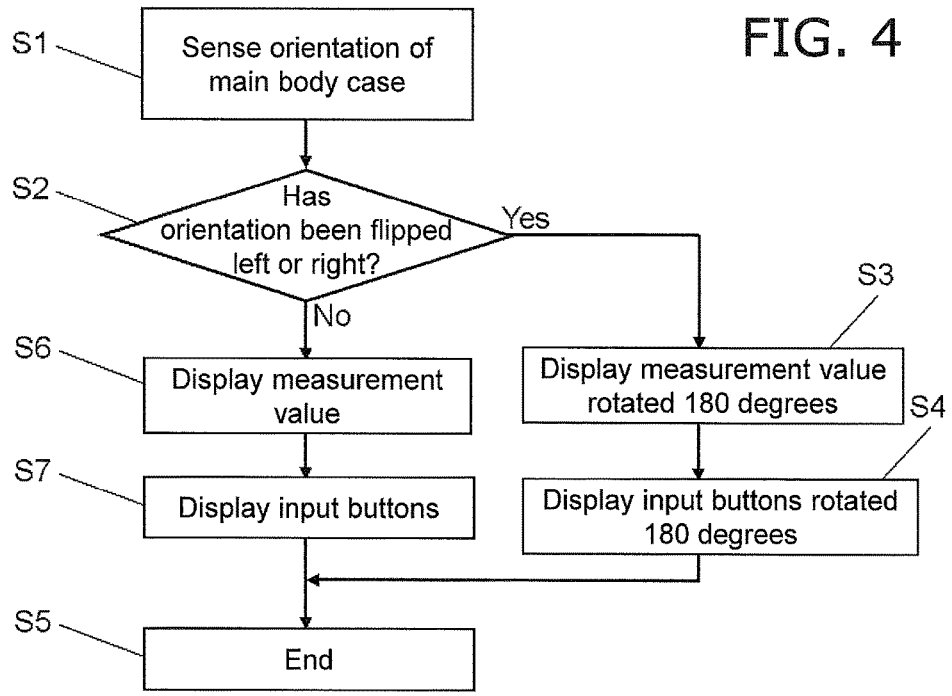
FIG. 4 is an operational flowchart of the biological sample measuring device in the first embodiment of the present invention.

In step S2 in FIG. 4, when the controller 6 has determined that the orientation of the main body case 1 is in the proper left-right state (in this embodiment, as shown in FIG. 1A, a state in which the sensor mounting component 3 is on the left side), the blood glucose level (measurement value) of the first display area 4a is displayed without being rotated (step S6 in FIG. 4), the input buttons in second display area 4b are displayed without being rotated (step S7 in FIG. 4), and the processing is ended (step S5 in FIG. 4).

Furthermore, in this embodiment, when the display of input buttons in the second display area 4b is rotated 180 degrees within the second display area 4b, the controller 6 displays the input buttons after a specific length of time. This results in a biological sample measuring device that is more convenient to use.

Specifically, when the biological sample measuring device goes from the state in FIG. 1A to FIG. 1B, the positional relation between the first display area 4a and the second display area 4b is flipped left and right between FIGS. 1A and 1B. In view of this, the display of the blood glucose level (measurement value) and the display of the input buttons are flipped left and right. The user takes the most interest in the blood glucose level (measurement value) out of the display on the display component 4. A blood glucose level of "234 mg/dL," which the user recognizes as being displayed on the left side of the display component 4 in the state in FIG. 1A, is not displayed on the left side of the display component 4 in the state in FIG. 1B, so the user may not recognize the blood glucose level right away.

Figure 5A:
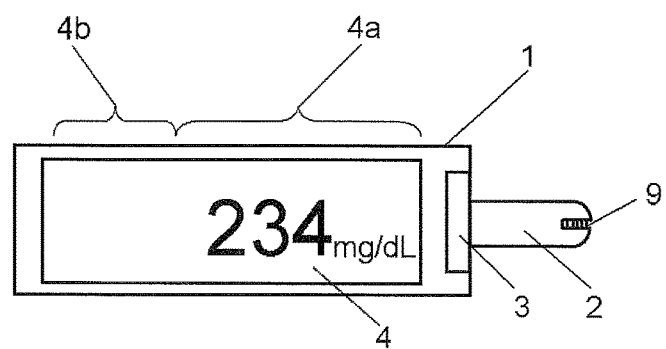
FIG. 5A is a plan view of the biological sample measuring device in the first embodiment of the present invention.

Accordingly, in this embodiment, when the display in the first display area 4a and the display in the second display area 4b are rotated 180 degrees within the respective display areas, the display component 4 displays as follows under the control of the controller 6. As shown in FIG. 5A, in step S3 in FIG. 4, first just the blood glucose level is displayed in the first display area 4a, and the input buttons are not displayed in the second display area 4b for a specific length of time (such as five seconds). Since there is a period in which only the blood glucose level (measurement value) is displayed on the display component 4, the user can properly read the display of a blood glucose level of "234 mg/dL" in the first display area 4a.

As shown in FIG. 5A, the controller 6 at this point displays a marker indicating the reading direction of the measured blood glucose level, in the first display area 4a. More specifically, the unit of "mg/dL" is displayed in small font at the lower rear of the display of the blood glucose level of "234" (that is, on the lower-right side of the display component 4 in FIG. 5). In this state, the display of the unit in small font serves as a marker indicating the reading direction. Therefore, the user can read "234 mg/dL" in the correct direction even when the display is only given in the first display area 4a.

Figure 5B:
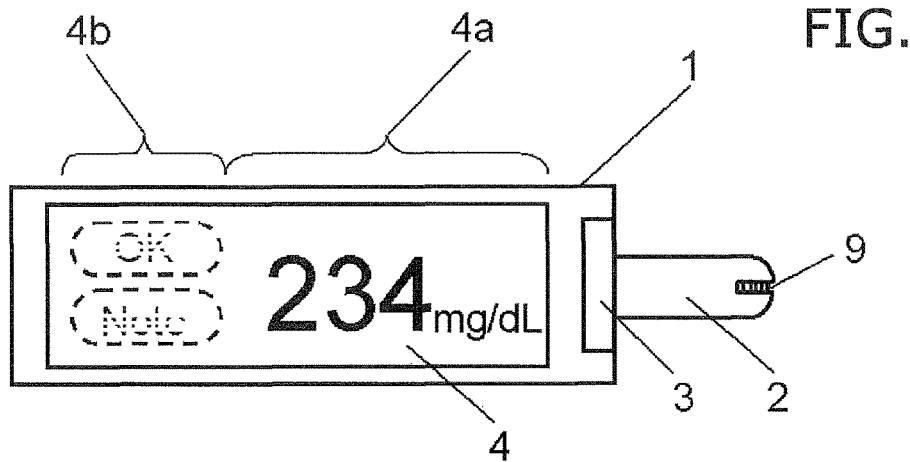
FIG. 5B is a plan view of the biological sample measuring device in the first embodiment of the present invention.
Figure 5C:
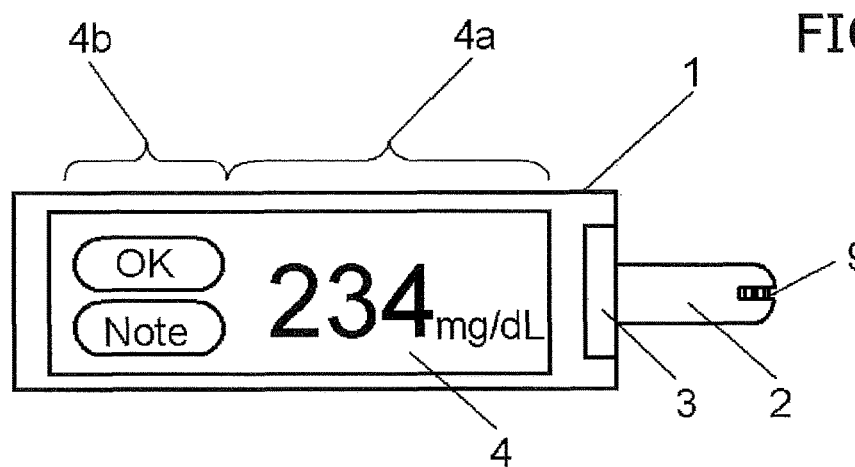
FIG. 5C is a plan view of the biological sample measuring device in the first embodiment of the present invention.

After this, in step S4 in FIG. 4, the display controller 11 of the controller 6 gradually displays input buttons in the second display area 4b over a period of 5 seconds, for example, as shown in FIGS. 5A to 5C.

That is, as described above, in this embodiment, when the main body case 1 is inverted left or right from the state in FIG. 1A to the state in FIG. 1B, the blood glucose level may be hard to see if the input buttons are displayed on the fore side of the display of the blood glucose level (measurement value) (the left side in FIGS. 5A to 5C), so first the blood glucose level is displayed, after which the input buttons are displayed.

In FIGS. 1A and 1B, the input buttons are the OK button and the Note button, which are displayed next to each other in a direction perpendicular to the lengthwise direction of the display component 4. In this embodiment, since this up/down combination is inverted integrally, the OK button will always be displayed above and the Note button below, whether in the state in FIG. 1A or the state in FIG. 1B.

Accordingly, after reliably reading the blood glucose level in the first display area 4a, the user can use the input buttons displayed in the second display area 4b to perform various functions.

This means that the input button can be properly operated after the blood glucose level has been reliably read. As a result, a more convenient biological sample measuring device can be provided.

When the input buttons are displayed, the controller 6 ends the series of processing (step S5 in FIG. 4).

Second Embodiment

In the biological sample measuring device according to the second embodiment, an input button enlargement mode is provided to the controller 6 of the biological sample measuring device in the first embodiment, which makes it easier to operate the input buttons when many of them are displayed in the second display area 4b.

Figure 6:
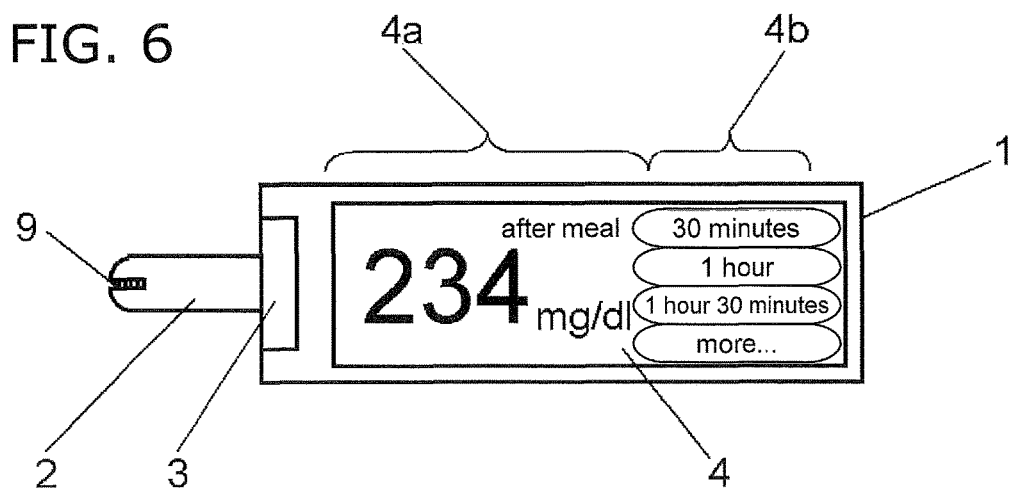
FIG. 6 is a plan view of the biological sample measuring device in a second embodiment of the present invention.

An example of the input button enlargement mode will be described. As shown in FIG. 6, the elapsed time from the last meal until measurement is an example of information recorded during the measurement of a blood glucose level. With the biological sample measuring device in this embodiment, the elapsed time that is recorded can be selected with a plurality of input buttons. More specifically, a plurality of input buttons are displayed in the second display area 4b as a "30 minutes" input button, a "one hour" input button, a "one hour and 30 minutes" input button, and a "more . . ." input button for selecting other times.

When many input buttons are thus displayed within the second display area 4b, each of the input buttons becomes smaller, which can make the buttons seem "difficult to operate" for the user.

Figure 7:
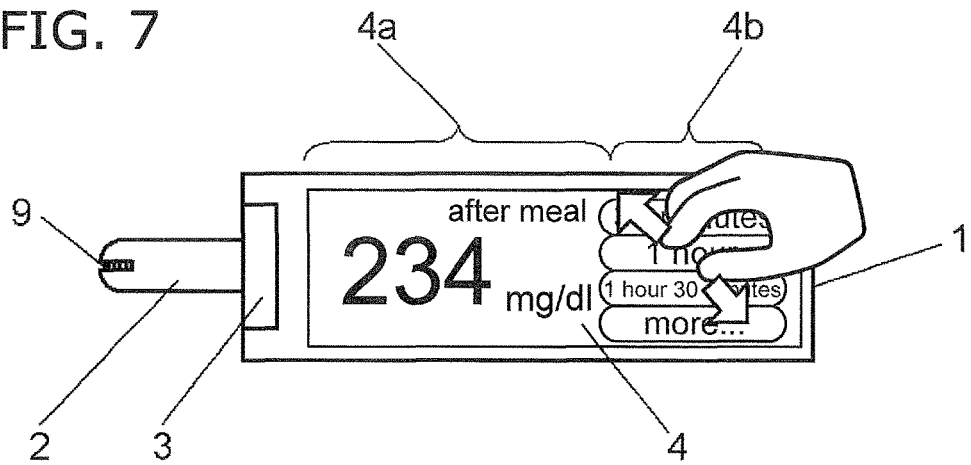
FIG. 7 is a plan view of the biological sample measuring device in the second embodiment of the present invention.
Figure 8:
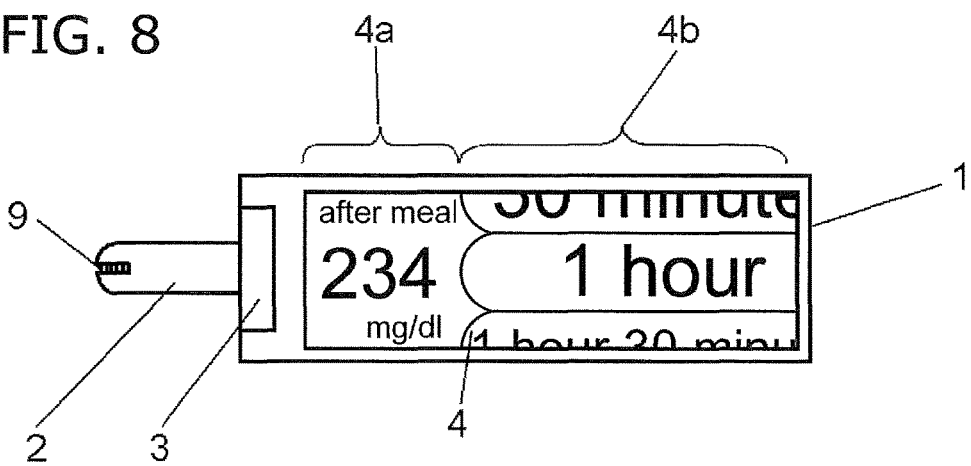
FIG. 8 is a plan view of the biological sample measuring device in the second embodiment of the present invention.

In view of this, in this embodiment, the input button enlargement mode is provided to the controller 6, and the input buttons are displayed enlarged as shown in FIGS. 7 and 8. This makes the buttons easier to operate.

To describe this in more specific terms, as shown in FIG. 7, when the user places his/her thumb and forefinger, for instance, against the second display area 4b at the same time and then spreads his/her thumb and forefinger apart, the input determination component 10 of the controller 6 determines this operation to be an enlargement instruction. In this embodiment, when this enlargement instruction is determined, the controller 6 switches to the input button enlargement mode.

As shown in FIG. 8, the display controller 11 is used to shrink the first display area 4a in the sensor mounting component 3 direction, and to enlarge the second display area 4b up to this shrunken portion. The input buttons themselves are also enlarged and displayed in this enlarged second display area 4b.

Therefore, the user can more easily operate the enlarged buttons.

At this point, the second display area 4b has a larger surface area than the first display area 4a, but the input buttons are displayed in the second display area 4b on the opposite side from the sensor mounting component 3 side. Therefore, the user's fingers, etc. will not touch the blood glucose level sensor 2 where blood has been deposited while the user is operating the input buttons.

Since the blood glucose level is displayed in a shrunken state in the shrunken first display area 4a at this point, the user can operate the input buttons while checking the display of the blood glucose level.

Depending on the user, even these enlarged input buttons may be seem to be "difficult to operate."

Figure 9:
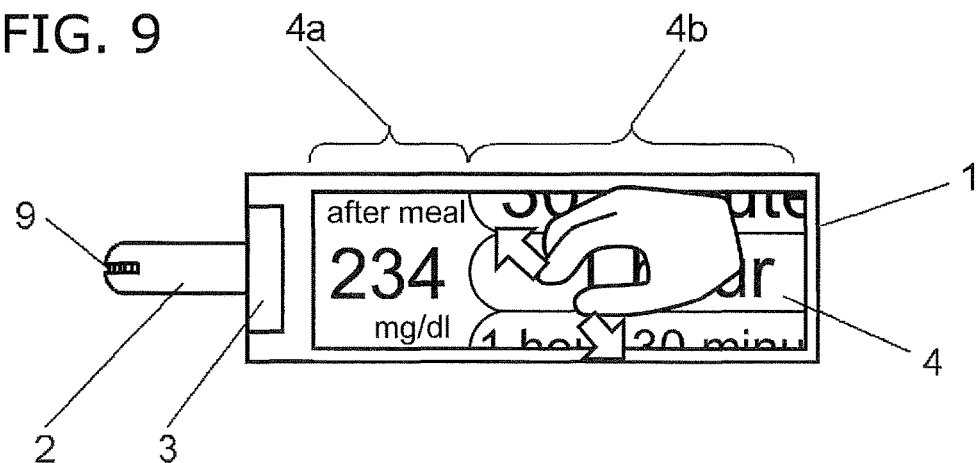
FIG. 9 is a plan view of the biological sample measuring device in the second embodiment of the present invention.
Figure 10:
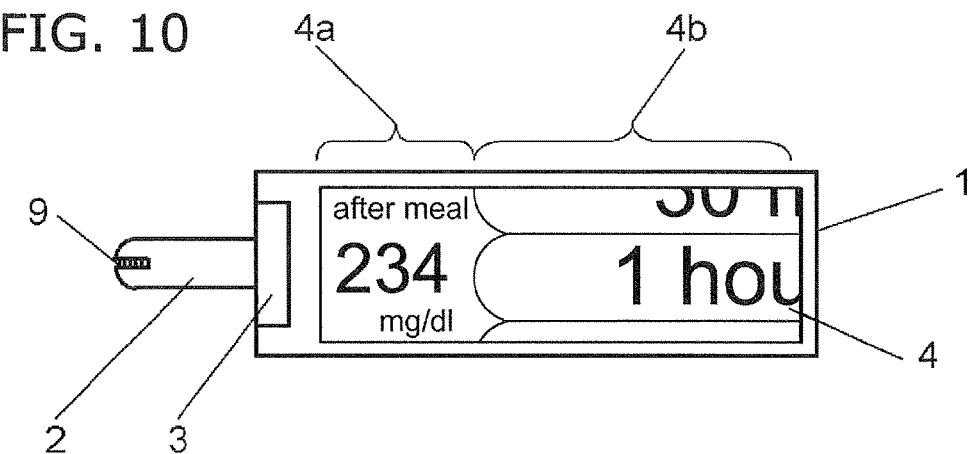
FIG. 10 is a plan view of the biological sample measuring device in the second embodiment of the present invention.

If this should happen, as shown in FIG. 9, the user can again place his/her thumb and forefinger against the second display area 4b and spread his/her thumb and forefinger apart, whereupon the input determination component 10 of the controller 6 will determine this operation to be an enlargement instruction. Then, as shown in FIG. 10, the input buttons are displayed enlarged within the range of the already enlarged second display area 4b.

Therefore, the user can more easily operate the enlarged input buttons.

On the other hand, although these repeated enlargements do make the input buttons easier to operate because they are displayed larger, the letters and numerals of the input buttons may end up being harder to see.

Figure 11:
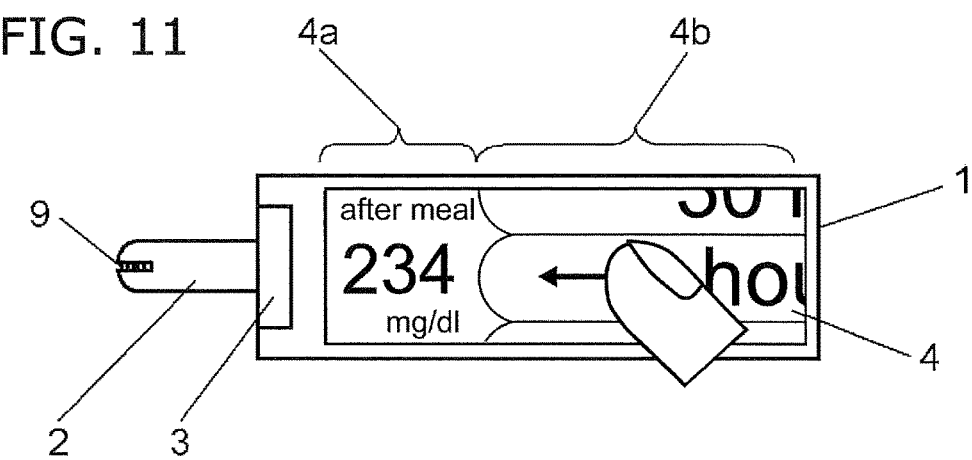
FIG. 11 is a plan view of the biological sample measuring device in the second embodiment of the present invention.

If this happens, as shown in FIG. 11, the user can place his forefinger against the second display area 4b, for example, and move this forefinger in the direction in which the input buttons are to be moved, whereupon the input determination component 10 of the controller 6 will determine this operation to be a scrolling instruction.

Figure 12:
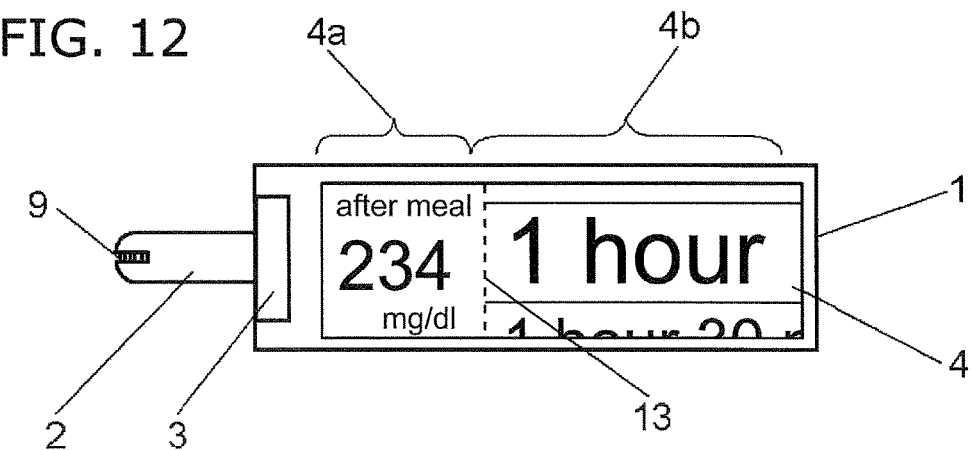
FIG. 12 is a plan view of the biological sample measuring device in the second embodiment of the present invention.

If this scrolling instruction is determined, the controller 6 scrolls the input buttons to the state shown in FIG. 12, for example. Accordingly, the user can identify the letters or numerals of the input buttons scrolled to the proper position.

This scrolling is performed within the already enlarged second display area 4b, so when the user operates an input button, his/her fingers, etc. will not touch the blood glucose level sensor 2 where blood has been deposited. As a result, the biological sample measuring device is more convenient to use.

As a result of this scrolling, part of the input buttons (in FIG. 12, for example, the left side of the input buttons) may be outside the second display area 4b and not displayed. In this state, part of the enlarged input buttons will disappear, which may cause some momentary confusion on the part of the user.

With this embodiment, however, if part of the enlarged input buttons should thus disappear, a boundary recognition line 13 will be displayed as a broken line between the shrunken first display area 4a and the enlarged second display area 4b.

Accordingly, the user will see this boundary recognition line 13 and realize that the input buttons are being displayed enlarged, and will realize that part of the enlarged input buttons has disappeared at this boundary recognition line 13.

Therefore, the disappearance of the input buttons will not cause any confusion on the part of the user.

Furthermore, in this embodiment, when the acceleration sensor 8 detects that the orientation of the main body case 1 is inverted to the left or right in the input button enlargement mode, the input button enlargement mode is ended, the shrunken first display area 4a is enlarged back to its original size, and the enlarged second display area 4b is shrunken back to its original size.

Figure 13:
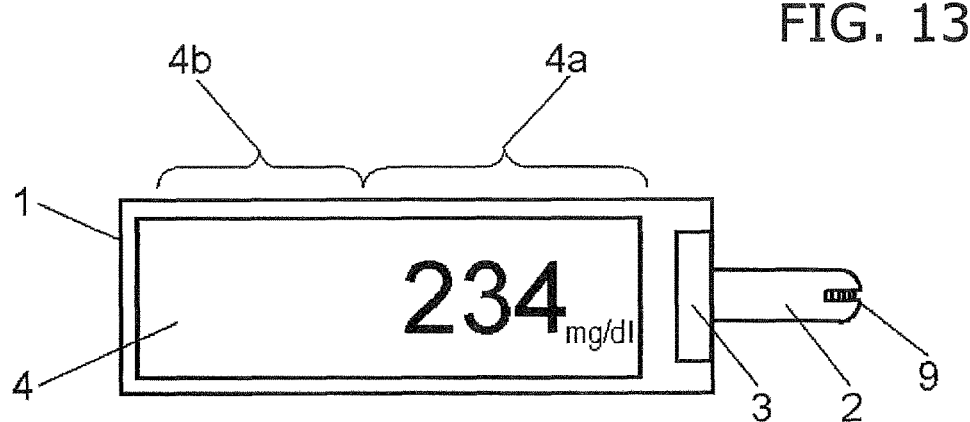
FIG. 13 is a plan view of the biological sample measuring device in the second embodiment of the present invention.

If the user inverts the orientation of the main body case 1 from the input button enlargement mode state shown in FIG. 12 to the state shown in FIG. 13, the sizes of the first display area 4a and the second display area 4b will return to their original states.

As shown in FIG. 13, the controller 6 first rotates the display of the blood glucose level (measurement value) 180 degrees, returns the display to its original size, and display the blood glucose level in the first display area 4a.

Figure 14:
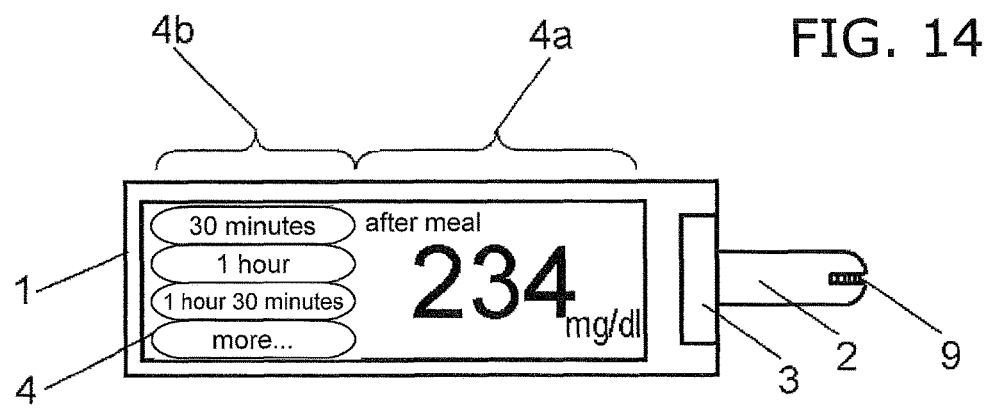
FIG. 14 is a plan view of the biological sample measuring device in the second embodiment of the present invention.

Once a specific amount of time has elapsed after this, the controller 6 gradually displays the input buttons in the second display area 4b as shown in FIG. 14. At this point, the input buttons are rotated 180 degrees and returned to their original display size.

Accordingly, just by inverting the orientation of the main body case 1, the user can return the display from the input button enlargement mode to the original display state, and therefore, can simply return the display to its original state. This makes a biological sample measuring device more convenient to use.

As shown in FIG. 14, in the first display area 4a, the blood glucose level and a marker indicating the reading direction (the notation of "mg/dL" in FIG. 14) are displayed in a state of having been rotated 180 degrees, but a notation describing the type of input buttons ("after meal" in FIG. 14) is displayed after being rotated 180 degrees and then moved to near the input buttons. In FIG. 6, the notation of "after meal" is disposed in the upper-right part of the first display area 4a, but in FIG. 14, in which the orientation of the main body case 1 has been inverted, the notation of "after meal" is disposed in the upper-left part of the first display area 4a. However, in both FIG. 6 and FIG. 14, the notation of "after meal" is disposed near the input buttons displayed in the second display area 4b, so the input buttons are easy to operate.

INDUSTRIAL APPLICABILITY

As described above, the present invention is expected to find wide application as a biological sample measuring device for measuring biological information such as blood glucose levels from blood, for example.

The invention claimed is:

1. A biological sample measuring device, comprising:
    a main body case including a sensor mounting component configured to mount a biological sample sensor at one end;
    a measurement component connected to the sensor mounting component, the measurement component disposed inside the main body case;
    a controller connected to the measurement component;
    an acceleration sensor connected to the controller and operable to sense an orientation of the main body case;
    a touch input-type display component provided to an outer surface of the main body case, the display component including a display;
    the display component divided into a first display area and a second display area by the controller;
    the first display area disposed on a sensor mounting component side and operable to display a measurement value;
    the second display area being disposed on an opposite side from the sensor mounting component side, and operable to display an input button operated by a user's touch input; and
    when the acceleration sensor has detected that the orientation of the main body case is inverted in a horizontal direction, the controller rotates a display of the measurement value in the first display area 180 degrees within the first display area, and rotates a display of the input button in the second display area 180 degrees within the second display area; and
    a plurality of input buttons in the second display area is provided after a specified length of time has elapsed after the controller rotates the display of the measurement value in the first display area 180 degrees within the first display area, the specified length of time being set to read the display of the measurement value and being a time greater than zero seconds.

2. The biological sample measuring device according to claim 1, wherein:
    when the controller rotates the display of the first display area 180 degrees within the first display area, a unit marker indicating a reading direction of the measurement value is displayed in the first display area.

3. The biological sample measuring device according to claim 2, wherein:
    the marker is a unit display that is displayed on a right side of the measurement value.

4. The biological sample measuring device according to claim 1, wherein:
    the controller has an input button enlargement mode in which an input button is enlarged, and
    in the input button enlargement mode:
        the first display area is shrunken in the sensor mounting component direction,
        the second display area is enlarged up to the shrunken first display area and is disposed on the opposite side from the sensor mounting component side, and
        the input button is enlarged in the enlarged second display area.

5. The biological sample measuring device according to claim 4, wherein:
    the controller scroll displays the input button in the enlarged second display area in the input button enlargement mode.

6. The biological sample measuring device according to claim 4, wherein:
    the controller controls the display to indicate that the input button has been enlarged in the input button enlargement mode.

7. The biological sample measuring device according to claim 6, wherein:
    the indication that the input button has been enlarged is a boundary recognition line between the shrunken first display area and the enlarged second display area.

8. The biological sample measuring device according to claim 4, wherein:
    when the acceleration sensor has detected that the orientation of the main body case is inverted in the horizontal direction in the input button enlargement mode, the controller ends the input button enlargement mode and returns the first display area and the second display area to their original sizes.

9. The biological sample measuring device according to claim 1, wherein:
    the plurality of input buttons in the second display area is provided after the specified length of time has elapsed after the controller rotates the display of the input button in the second display area 180 degrees within the second display area.

* * * * *